United States Patent
Ta et al.

(10) Patent No.: US 8,882,826 B2
(45) Date of Patent: Nov. 11, 2014

(54) INTRAVASCULAR STENT

(75) Inventors: Diem Uyen Ta, San Jose, CA (US);
David Chi, San Francisco, CA (US);
Svava Maria Atladottir, San Francisco, CA (US); Bjorn Svensson, Gilroy, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 11/841,291

(22) Filed: Aug. 20, 2007

(65) Prior Publication Data
US 2008/0051876 A1    Feb. 28, 2008

Related U.S. Application Data

(60) Provisional application No. 60/823,239, filed on Aug. 22, 2006.

(51) Int. Cl.
*A61F 2/06* (2013.01)
*A61F 2/915* (2013.01)
*A61F 2/91* (2013.01)

(52) U.S. Cl.
CPC ......... *A61F 2/915* (2013.01); *A61F 2250/0029* (2013.01); *A61F 2002/91525* (2013.01); *A61F 2/91* (2013.01); *A61F 2002/91558* (2013.01); *A61F 2002/91575* (2013.01); *A61F 2002/91508* (2013.01)
USPC ....................................... 623/1.16

(58) Field of Classification Search
USPC ............................... 623/1.15, 1.16
See application file for complete search history.

(56) References Cited

U.S. PATENT DOCUMENTS

| | | | |
|---|---|---|---|
| 2,978,787 | A | 4/1961 | Leibig |
| 2,990,605 | A | 7/1961 | Densyk |
| 3,029,819 | A | 4/1962 | Starks |
| 3,096,560 | A | 7/1963 | Liebig |
| 3,142,067 | A | 7/1964 | Liebig |
| 3,657,744 | A | 4/1972 | Ersek |
| 3,908,662 | A | 9/1975 | Razgulov et al. |

(Continued)

FOREIGN PATENT DOCUMENTS

| | | |
|---|---|---|
| DE | 91 02 312 U1 | 6/1992 |
| DE | 19913978 A1 | 9/2000 |

(Continued)

OTHER PUBLICATIONS

Lawrence, David D., Jr., M.D., et al. Percutaneous Endovascular Graft: Experimental Evaluation, *Radiology*, vol. 163, No. 2, pp. 357-360 (1987).

(Continued)

*Primary Examiner* — Kathleen Holwerda
*Assistant Examiner* — Sarah Simpson
(74) *Attorney, Agent, or Firm* — Fulwider Patton LLP

(57) ABSTRACT

An expandable stent for implanting in a body lumen, such as a coronary artery, peripheral artery, or other body lumen. In one aspect, the stent includes a butterfly pattern to which connecting links are attached. In another aspect, the stent embodies a non-directional structure. One embodiment is a stent in which one or both ends are more flexible than the center portion. Also, the stent may have a non-uniform drug coating. Another embodiment relates to a stent having ends that are more radiopaque than the center portion.

18 Claims, 12 Drawing Sheets

(56) References Cited

U.S. PATENT DOCUMENTS

| | | | |
|---|---|---|---|
| 3,945,052 A | 3/1976 | Liebig | |
| 4,041,931 A | 8/1977 | Elliott et al. | |
| 4,047,252 A | 9/1977 | Liebig et al. | |
| 4,061,134 A | 12/1977 | Samuels et al. | |
| 4,108,161 A | 8/1978 | Samuels et al. | |
| 4,140,126 A | 2/1979 | Choudhury | |
| 4,193,137 A | 3/1980 | Heck | |
| 4,202,349 A | 5/1980 | Jones | |
| 4,214,587 A | 7/1980 | Sakura, Jr. | |
| 4,517,687 A | 5/1985 | Liebig et al. | |
| 4,560,374 A | 12/1985 | Hammerslag | |
| 4,562,596 A | 1/1986 | Kornberg | |
| 4,577,631 A | 3/1986 | Kreamer | |
| 4,617,932 A | 10/1986 | Kornberg | |
| 4,652,263 A | 3/1987 | Herweck et al. | |
| 5,807,404 A * | 9/1998 | Richter | 623/1.16 |
| 6,159,238 A | 12/2000 | Killion | |
| 6,165,195 A | 12/2000 | Wilson et al. | |
| 6,183,509 B1 | 2/2001 | Dibie | |
| 6,203,568 B1 | 3/2001 | Lombardi et al. | |
| 6,210,429 B1 | 4/2001 | Vardi et al. | |
| 6,221,098 B1 | 4/2001 | Wilson et al. | |
| 6,254,593 B1 | 7/2001 | Wilson | |
| 6,258,116 B1 | 7/2001 | Hojeibane | |
| 6,264,682 B1 | 7/2001 | Wilson et al. | |
| 6,290,673 B1 | 9/2001 | Shanley | |
| 6,325,826 B1 | 12/2001 | Vardi | |
| 6,346,089 B1 | 2/2002 | Dibie | |
| 6,358,274 B1 | 3/2002 | Thompson | |
| 6,361,555 B1 | 3/2002 | Wilson | |
| 6,629,994 B2 * | 10/2003 | Gomez et al. | 623/1.15 |
| 6,805,898 B1 | 10/2004 | Wu et al. | |
| 6,846,323 B2 * | 1/2005 | Yip et al. | 623/1.16 |
| 7,090,694 B1 | 8/2006 | Morris et al. | |
| 2001/0029397 A1 | 10/2001 | Thompson | |
| 2001/0037137 A1 | 11/2001 | Vardi et al. | |
| 2001/0049548 A1 | 12/2001 | Vardi et al. | |
| 2001/0056297 A1 | 12/2001 | Hojeibane | |
| 2002/0058989 A1 | 5/2002 | Chen et al. | |
| 2002/0198593 A1 | 12/2002 | Gomez et al. | |
| 2003/0036793 A1 | 2/2003 | Richter et al. | |
| 2003/0097169 A1 | 5/2003 | Brucker et al. | |
| 2003/0125802 A1 | 7/2003 | Callol et al. | |
| 2003/0139796 A1 | 7/2003 | Sequin et al. | |
| 2003/0139803 A1 | 7/2003 | Sequin et al. | |
| 2003/0167083 A1 | 9/2003 | Lashinski et al. | |
| 2003/0195606 A1 * | 10/2003 | Davidson et al. | 623/1.11 |
| 2004/0044400 A1 * | 3/2004 | Cheng et al. | 623/1.16 |
| 2004/0127977 A1 | 7/2004 | Shanley | |
| 2004/0230293 A1 | 11/2004 | Yip et al. | |
| 2004/0243218 A1 * | 12/2004 | Schaeffer | 623/1.15 |
| 2005/0004657 A1 * | 1/2005 | Burgermeister | 623/1.16 |
| 2005/0043782 A1 | 2/2005 | Gomez et al. | |
| 2005/0222670 A1 * | 10/2005 | Schaeffer | 623/1.15 |
| 2006/0020322 A1 | 1/2006 | Leynov et al. | |
| 2006/0036312 A1 | 2/2006 | Tomonto | |
| 2006/0100695 A1 | 5/2006 | Peacock, III et al. | |
| 2008/0009932 A1 | 1/2008 | Ta et al. | |
| 2008/0051876 A1 | 2/2008 | Ta | |
| 2008/0086190 A1 | 4/2008 | Ta | |

FOREIGN PATENT DOCUMENTS

| | | |
|---|---|---|
| EP | 0 461 791 A1 | 12/1991 |
| EP | 0 466 518 A3 | 1/1992 |
| EP | 0747 020 A2 | 12/1996 |
| EP | 0 804 907 A2 | 11/1997 |
| EP | 0 897 700 A1 | 2/1999 |
| EP | 0 904 745 A2 | 3/1999 |
| EP | 1236445 A2 | 9/2002 |
| EP | 1277449 A1 | 1/2003 |
| FR | 2673843 A1 | 9/1992 |
| FR | 2737969 A1 | 2/1997 |
| JP | 2003724 A | 1/1990 |
| JP | 2002102358 A | 4/2002 |
| SU | 1217402 A | 3/1986 |
| SU | 1318235 A1 | 6/1987 |
| SU | 1389778 A2 | 4/1988 |
| SU | 1457921 A1 | 2/1989 |
| SU | 1482714 A2 | 5/1989 |
| WO | WO 95/16406 A1 | 6/1995 |
| WO | WO 95/21592 A1 | 8/1995 |
| WO | WO 96/23455 A1 | 8/1996 |
| WO | WO 96/24306 A1 | 8/1996 |
| WO | WO 96/24308 A1 | 8/1996 |
| WO | WO 96/34580 A1 | 11/1996 |
| WO | WO 97/07752 A1 | 3/1997 |
| WO | WO 97/15346 A1 | 5/1997 |
| WO | WO 97/16217 A1 | 5/1997 |
| WO | WO 97/418043 A1 | 11/1997 |
| WO | WO 97/45073 A1 | 12/1997 |
| WO | 9822159 A2 | 5/1998 |
| WO | WO 98/19628 A1 | 5/1998 |
| WO | WO 98/36709 A1 | 8/1998 |
| WO | WO 99/04726 A1 | 2/1999 |
| WO | 9915108 A2 | 4/1999 |
| WO | WO 00/07523 A1 | 2/2000 |
| WO | 0062710 A | 10/2000 |
| WO | WO 01/21095 A2 | 3/2001 |
| WO | 0215824 A2 | 2/2002 |
| WO | WO 02/068012 A1 | 9/2002 |

OTHER PUBLICATIONS

Yoshioka, Tesuya, et al., Self-Expanding Endovascular Graft: An Experimental Study in Dogs, *Radiology*, vol. 170, pp. 673-676 (1989).

Mirich, David, M.D., et al., Percutaneously Placed Endovascular Grafts for Aortic Aneurysms: Feasibility Study, *Radiology*, vol. 170, No. 3, Part 2, pp. 1033-1037 (1989).

Parodi, J.C., M.D., et al., Transfemoral Intraluminal Graft Implantation for Abdominal Aortic Aneurysms, *Annals of Vascular Surgery*, vol. 5, No. 6, pp. 491-499 (1991).

Chuter, Timothy A.M., et al., Transfemoral Endovascular Aortic Graft Placement, *Journal of Vascular Surgery*, pp.185-196 (Aug. 1993).

Bard XT Carina Bifurcate Stent (Brochure) (Undated).

U.S. Appl. No. 11/507,852, filed Aug. 22, 2006; Amendment/RCE filed on Jan. 21, 2010.

* cited by examiner

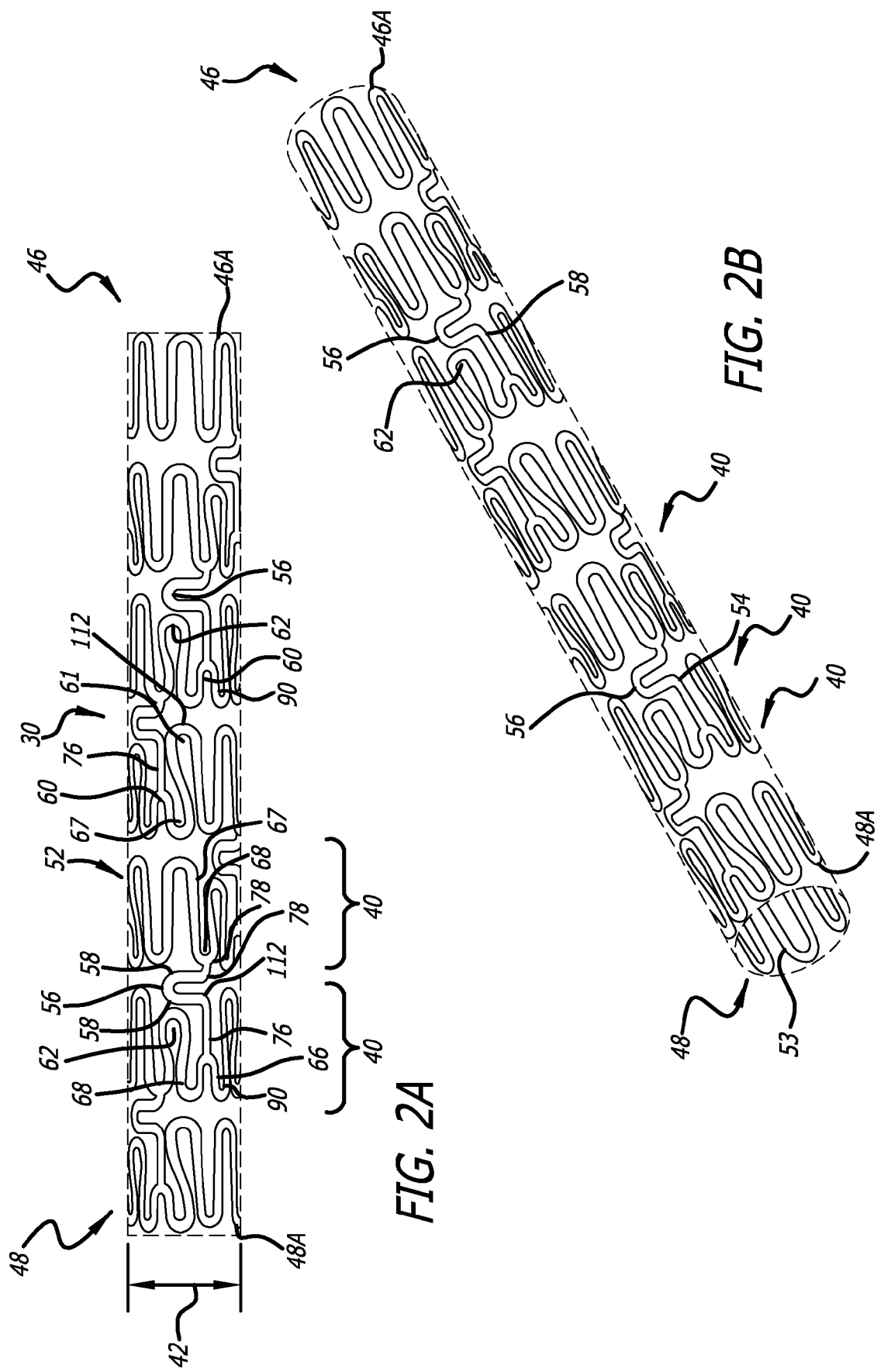

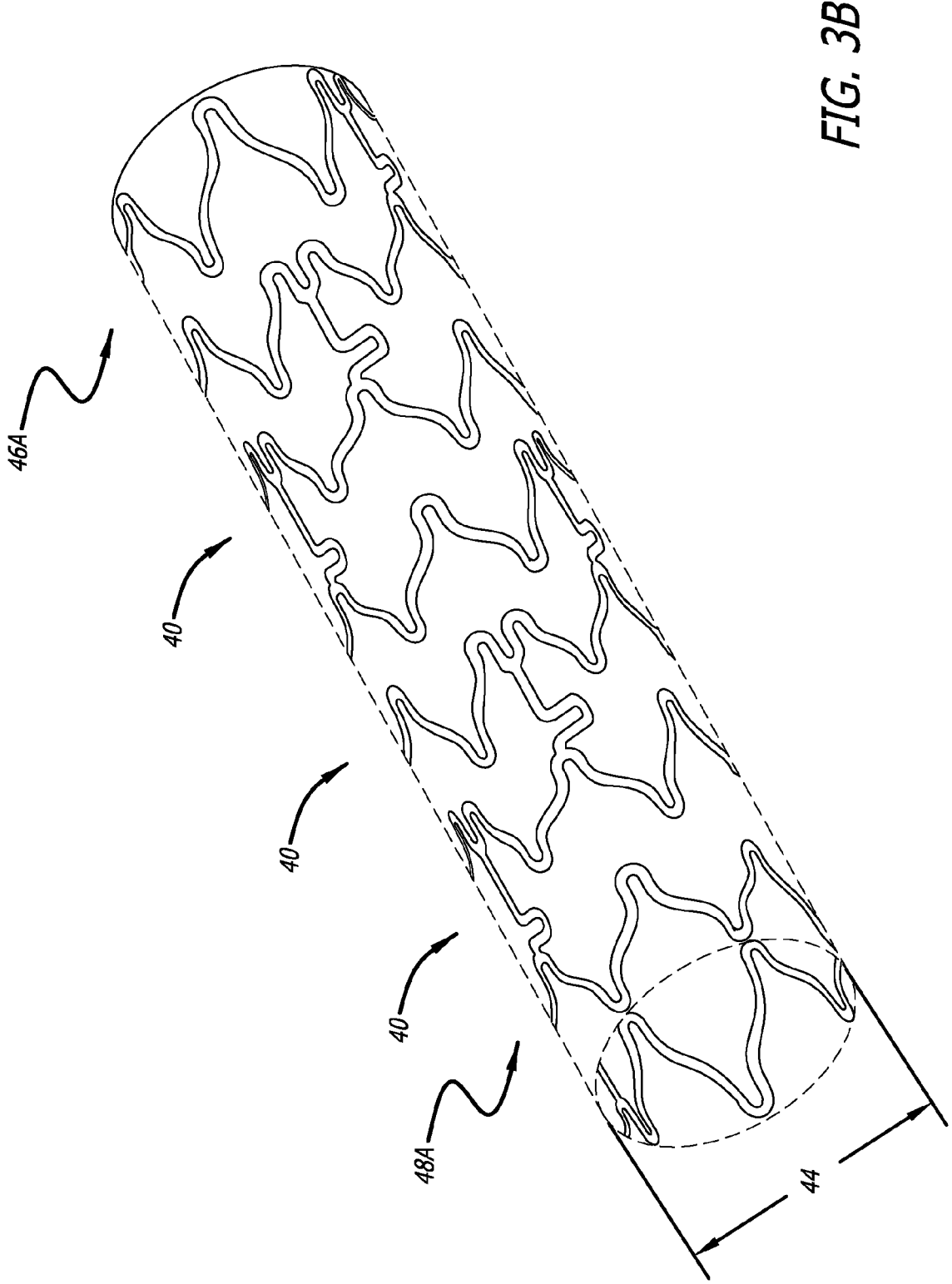

INTRAVASCULAR STENT

CROSS-REFERENCES TO RELATED APPLICATIONS

This application is based upon U.S. Provisional Application No. 60/823,239.

BACKGROUND OF THE INVENTION

The invention relates to vascular repair devices and, in particular, to an approach for designing intravascular stents in which the flexibility profile, the drug coating and/or the radiopacity are modified to meet specific design goals.

Stents are generally tubular-shaped devices which function to hold open a segment of a blood vessel. They also are suitable for use to support and hold back a dissected arterial lining that can occlude the fluid passageway. That is, whether self-expanding or expandable using force, stents are delivered within vasculature in a radially compressed configuration and then implanted at an interventional site while assuming a radially expanded configuration. At present, there are numerous commercial stents being marketed throughout the world. For example, some known prior art stents have multiple cylindrical rings connected by one or more links. While some of these stents are flexible and have the appropriate radial rigidity needed to hold open a blood vessel, there typically is a tradeoff between flexibility and radial strength and the ability to be tightly compressed or crimped onto a catheter so that it does not move relatively to the catheter or dislodge prematurely prior to controlled implantation at an interventional site.

Various conventional stents can include a plurality of rings connected by links. In certain stents, the rings include a plurality of peaks and valleys connected by bar arms. When these rings are positioned in phase relatively to one another, W-crests and Y-crests are formed at the points of connection between the links and rings. Once a stent embodying this structure is implanted at an interventional site, a significant amount of strain is placed upon the peaks and valleys. In fact, the link can become angulated or twisted upon stent expansion resulting in an overall twisted stent configuration. Such a twisted stent configuration can suffer from inadequate vessel wall apposition and thus, may not perform optimally in holding a vessel open. Further, the degree of twisting often cannot be predicted due to manufacturing and material variability which consequently limits the reliability of stent function.

Other factors also contribute to the unpredictability of stent performance. That is, conventional stents embody a pattern of links and rings which can be characterized as directional in configuration. A typical stent can include a pattern of adjacently arranged rings which extend the length of a stent and includes a first end which differs from that of a second end of the stent. Due to this directional structure, such a stent must be placed upon a catheter in a particular direction so that when it is deployed and implanted within vasculature, the stent will be arranged as contemplated to achieve expected performance. Unfortunately, conventional stents embodying directional structure can be placed on a catheter incorrectly due to operator error, and it is difficult to either identify this error or to correct it during a surgical procedure.

Conventional stents can also be typically designed to have a relatively uniform flexibility across the length of the stent. However, this uniform flexibility is often not optimal for moving the stent through curved portions of the body. Accordingly, what has been needed and heretofore unavailable is a stent that is particularly more flexible at one or both ends than the center portion of the stent for better movement through the body.

Additionally, conventional stents tend to have a uniform drug coating. This can be problematic when, for example, the physician overlaps stents. Accordingly, what has been needed and heretofore unavailable is a stent that has greater drug coating on the center portion of the stent as compared to one or both ends of the stent. It can be particularly desirable to combine this non-uniform drug coating with a stent having superior flexibility at one or both ends, as described above.

Further, conventional stents tend to be uniformly radiopaque. However, this uniformity can present problems when, for example, a physician overlaps stents and needs to better monitor the overlapped regions of the stent. Consequently, what has been needed and heretofore unavailable is a stent that has enhanced radiopaque properties at one or both ends of the stent, as compared to the center portion of the stent.

Accordingly, what is needed is a stent including structure which provides desired flexibility without compromising radial strength and reduces unwanted stresses and twisting. Also, there is a need for a stent which addresses problems associated with directional stents. Moreover, there is a need for a stent which addresses problems associated with stent on satisfies these and other needs. The present invention satisfies these and other needs.

SUMMARY OF THE INVENTION

The present invention is directed to an intravascular stent including structure enhancing flexibility without compromising radial strength and minimizing twisting and inherent stresses. The present invention is also directed towards a stent incorporating a non-directional pattern of rings and links.

In one aspect, the invention includes a flexible intravascular stent for use in a body lumen, comprising a plurality of cylindrical rings aligned along a common longitudinal axis and interconnected to form the stent, each cylindrical ring having a first delivery diameter and a second larger implanted diameter. Each cylindrical ring includes an open W or butterfly pattern to which one end of a link between adjacent rings is connected. Further, each ring includes a plurality of first peaks, second peaks, and third peaks, adjacent third peaks defining the butterfly pattern. Each of the peaks has a height and an apex, the first peaks being taller than the second peaks, and the second peaks being taller than the third peaks. Described in another way, each cylindrical ring has a plurality of first valleys, second valleys, and third valleys, adjacent third valleys forming the butterfly pattern. Moreover, each of the valleys has a depth and an apex, the first valleys being deeper than the second valleys, and the second valleys being deeper than the third valleys.

At least one link attaches each cylindrical ring to an adjacent cylindrical ring. The links can include an undulation having a curved portion extending transverse to the stent longitudinal axis toward the second peak. Additionally, the curved portion of the undulating link can be longitudinally aligned with the second peak. Also, each undulating link can include an arm that is straight and parallel to the longitudinal axis of the stent and which is circumferentially offset from the second peak.

The invention further contemplates peaks and valleys having a different radii and/or heights than other or adjacent peaks and valleys. In still another aspect of the invention, at least a portion of the links or cylindrical rings can have a variable thickness configuration and/or a variable width.

Still another aspect of the invention is directed towards a non-directional stent. Such a stent is not required to be mounted onto a stent delivery system in a particular proximal-distal orientation. The configuration of peaks and valleys at a proximal end of the stent is generally a mirror image of the configuration of peaks and valleys at the distal end. Both the proximal end and the distal end cylindrical rings may include various combinations of tall peaks, intermediate peaks, short peaks, deep valleys, intermediate valleys, and shallow valleys. Further, the non-directional stent can include the open W or butterfly pattern. In one embodiment, at least two of the open W or butterfly pattern configurations face in opposite directions from each other along the length of the stent. In addition, it is contemplated that not all of the curved portions of the undulating links face in the same direction in the non-directional stent. Because the proximal and distal ends of the stent are generally mirror image configurations or a rotated mirror image of the opposite end of the stent, and the configuration of peaks and valleys of the rings is reversed at one or more points along the length of the stent, the non-directional stent may be mounted onto a stent delivery system in either direction.

The present invention is also directed to an intravascular stent with customized flexibility, drug coating and/or radiopacity properties. In one embodiment, the present invention is directed towards a stent with proximal and/or distal ends that are more flexible than the center portion of the stent. This design may also have a drug coating, in which the drug coating is greater at the center of the stent than at the ends. One or more ends of the stent may be more radiopaque than the center portion of the stent.

Considering one aspect, the invention includes a stent in which one or both ends are more flexible than the center portion, and a drug coating that is greater on the center portion than at the ends. Consequently, a flexible intravascular stent for use in a body lumen has a plurality of cylindrical rings aligned along a common longitudinal axis. At least one link connects adjacent cylindrical rings. The stent has a first end portion, a center portion, and a second end portion, with at least one of the end portions being more flexible than the center portion. The stent has a drug coating, the drug coating having greater coverage on the center portion than on at least one of the end portions.

This embodiment may have one or more of the following aspects. Both ends may be more flexible than the center portion. At least one connecting link in one or both of the end portions may be very flexible with, for example, a shape that increases flexibility, such as a shape with multiple turns. At least one or more cylindrical rings in at least one end portion comprises peaks of uniform extent. One or more cylindrical rings in at least one end portion may have members with a "U" or "Y" profile. At least one link in the center portion may have a "U" profile. At least one cylindrical ring in the center portion may have at least one member with a butterfly pattern.

According to another aspect of the invention, a stent may have one end that is more flexible than the rest of the stent. This will typically be the distal end of the stent which, when flexing through a curve in the body, is the leading edge of the stent and after which the rest of the stent will follow. Such a stent has a plurality of cylindrical rings aligned along a common longitudinal axis. At least one link connects adjacent cylindrical rings. The stent has a first end portion, a center portion, and a second end portion. At least one of the end portions is more flexible than the center portion.

According to another aspect of the invention, a stent has at least one end that is more radiopaque than the center portion. Such a stent has a plurality of cylindrical rings aligned along a common longitudinal axis. At least one link connects adjacent cylindrical rings. The stent has a first end portion, a center portion, and a second end portion. At least one of the end portions is more radiopaque than the center portion.

This type of stent may have a design with greater surface area density at one or both of the end portions than at the center portion. Consequently, for a metal stent, an end portion that has the greater surface area density will be more radiopaque than the center portion.

The present invention therefore provides the stent designer with options for customizing a stent design so as to meet design requirements for a given environment within the body and/or for particular patient requirements.

Various features recited above may be employed individually, or in combination with other features. Further features and advantages of the present invention will become more apparent from the following detailed description of the invention, when taken in conjunction with the accompanying exemplary drawings.

BRIEF DESCRIPTION OF THE DRAWINGS

The invention is herein described, by way of example only, with reference to the accompanying drawings, wherein:

FIG. 2A is a plan view of a portion of the stent of FIG. 1 forming a radially compressed cylindrical configuration.

FIG. 2B is a perspective view of a portion of the stent of FIG. 2A.

FIG. 3B is a perspective view of a portion of the stent of FIG. 1 in a cylindrical configuration and illustrating the rings and links in an expanded configuration.

DETAILED DESCRIPTION OF THE PREFERRED EMBODIMENTS

Figure 1:
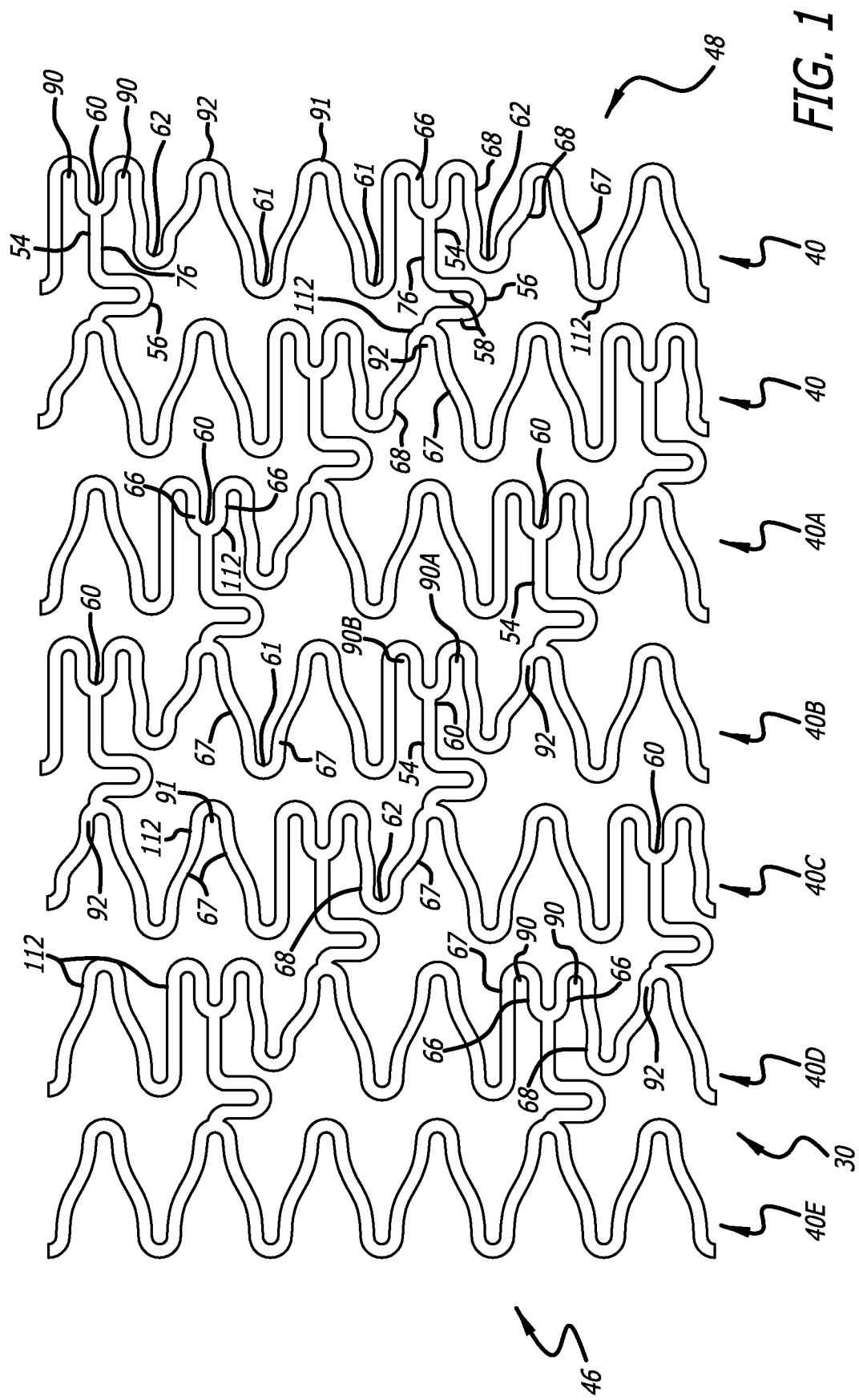
FIG. 1 is a plan view of a portion of a flattened stent of one embodiment of the invention which illustrates a pattern of rings and links.

Referring to the drawings, which are provided for purposes of illustration and by way of example but not limitation, the present invention is illustrated in FIGS. 1-9B.

Turning now to FIG. 1, an exemplary stent 30 of the present invention is shown in a flattened condition so that the pattern can be clearly viewed, even though the stent is in a cylindrical form in use, such as shown in FIGS. 2A-B. The stent is typically formed from a tubular member, however it can be formed from a flat sheet such as shown in FIG. 1 and rolled into a cylindrical configuration.

Figure 3A:
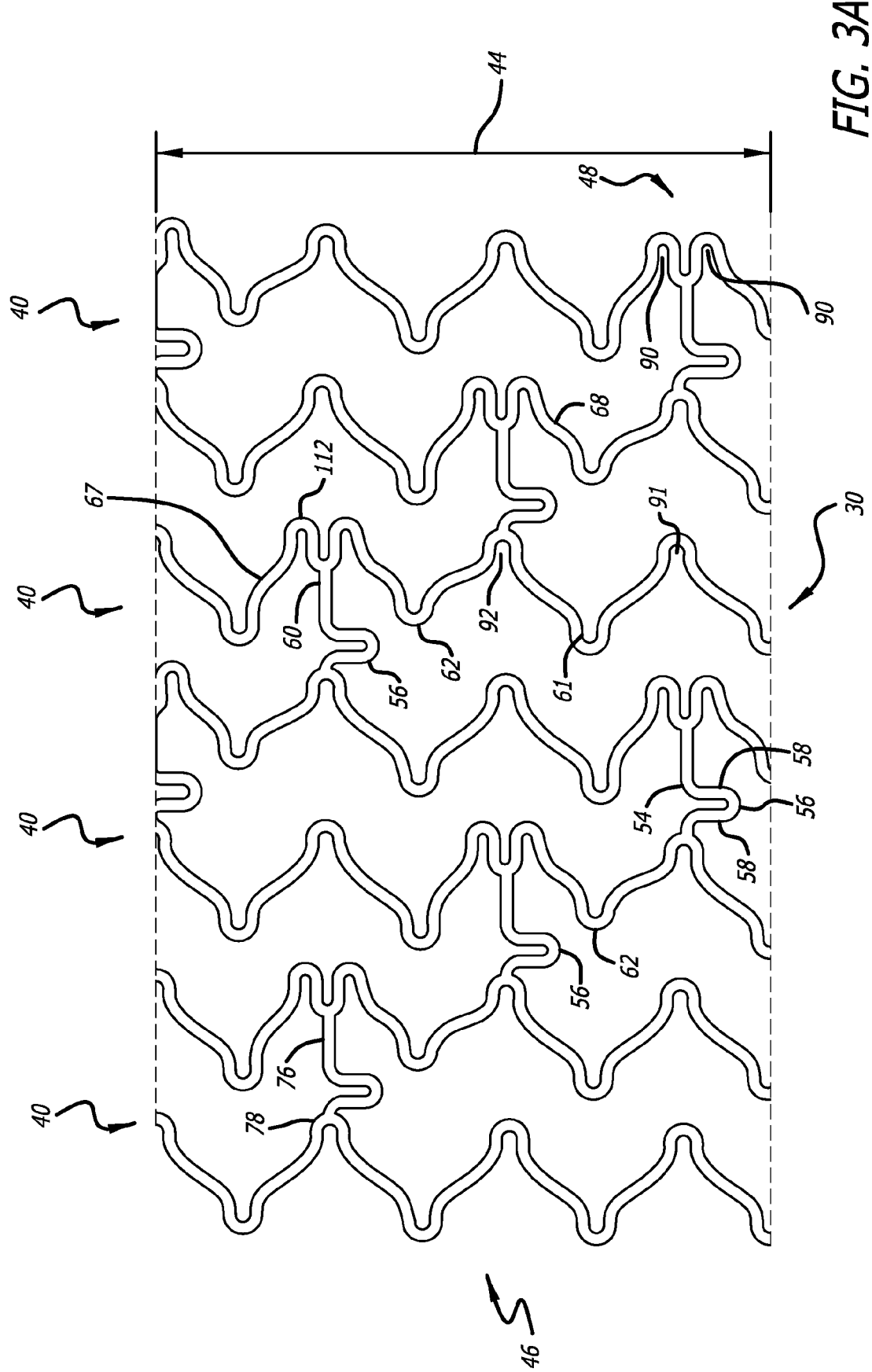
FIG. 3A is a plan view of a portion of the stent of FIG. 1 in a flattened configuration and illustrating the rings and links in an expanded configuration.

As shown in FIGS. 1-3B, stent 30 is made up of a plurality of cylindrical rings 40 which extend circumferentially around the stent. It is to be recognized that there may be fewer or more cylindrical rings than is shown in the illustrated drawings. The rings are aligned along a common longitudinal axis and interconnected by links 54 to form the stent. The links 54 can be generally straight members (See FIG. 5) or can include one or more curves or turns as shown in the figures. Moreover, links with undulation can be configured at all locations or any selected locations along the stent. The stent has a delivery diameter 42 (FIG. 2A), and expands to an implanted diameter 44 (FIGS. 3A and 3B). The stent has a proximal end 46 and a distal end 48. Typically, since the stent is contemplated to be laser cut from a tube, there are no discreet parts.

Referring specifically to FIG. 2B, each cylindrical ring includes a cylindrical outer wall surface 52 which defines the outermost surface of the stent and a cylindrical inner wall surface 53 which defines the innermost surface of the stent. The links 54 connect one cylindrical ring 40 to an adjacent cylindrical ring 40. To prevent links 54 from compromising the longitudinal flexibility of the stent, a curved portion 56 is incorporated into link 54. This curved portion 56 is connected to one or more substantially straight portions 58 wherein the straight portions 58 are substantially perpendicular to the longitudinal axis of the stent. Thus, as the stent is being delivered through a tortuous vessel, such as a coronary artery, the curved portions 56 and straight portions 58 of the undulating links will permit the stent to flex in the longitudinal direction which substantially enhances delivery of the stent to the target site. The number of bends and straight portions in a link can be increased or decreased from that shown to achieve different flexibility constructions. In one embodiment (not shown), it is contemplated that the links can comprise a plurality of curved portions and straight portions 58. With the straight portions being substantially perpendicular to the stent longitudinal axis, the link 54 acts much like a hinge at the curved portion 56 to provide flexibility in both crimped and expanded states. The number of links 54 can be adjusted to vary the longitudinal flexibility in the crimped and expanded states of a stent.

The stent 30 further can be described as having rings including a plurality of alternative peaks and valleys. The peaks and valleys can have similar or different sizes. In one embodiment, the rings can include one or more open W or butterfly patterns of struts to which links between adjacent rings are connected. Accordingly, the rings can include a plurality of short peaks 60, tall peaks 61, intermediate peaks 62, shallow valleys 90, deep valleys 91, and intermediate valleys 92. The peaks and valleys are formed from various length struts and apices 112. In one embodiment, the struts include short struts 66, long struts 67, and intermediate struts 68. The lengths of these struts can be varied to achieve a desired expansion diameter. As shown, each open W or butterfly pattern is defined by one short peak 60, two short struts 66, one long strut 67 and one intermediate strut 68. The struts can be either curved or straight depending upon a particular application. Also, as shown, each peak has a height, the tall peaks being taller than the intermediate peaks, and the intermediate peaks being taller than the short peaks. Additionally, each valley has a depth, the deep valleys being deeper than the intermediate valleys, and the intermediate valleys being deeper than the shallow valleys. In other embodiments, a greater range in the types of heights of peaks and/or a greater range in the types of depths of valleys may be included, as explained in further detail below with references to FIG. 5.

Additionally, in one aspect, the stent 30 can further include one or more Y patterns of struts. With reference to FIG. 2A, the Y pattern is defined by one intermediate valley 92, one long strut 67, and one intermediate strut 68.

It is also contemplated that a stent of the present invention can further include at least one additional peak (not shown) having a different height than the short peak, the tall peak, and the intermediate peak. Also, the stent can further include at least one additional valley (not shown) having a different depth than the shallow valley, the intermediate valley, and the deep valley. For example, one embodiment may have four different height peaks and four different depth valleys. Moreover, the number of peaks and valleys can vary in number for each ring depending upon the application. Thus, for example, if the stent is to be implanted in a coronary artery, a lesser number of peaks and valleys are required than if the stent is implanted in a peripheral artery, which has a larger diameter than a coronary artery. Moreover, the number of peaks and valleys can be adjusted to vary the expansion diameter. Furthermore, the order or juxta-positioning of various sized peaks and valleys can be varied within a ring or from one ring to another, and the various peaks and valleys of adjacent rings can be aligned or offset from each other. It is to be understood that the definition of an open W pattern should not be limited but generally should imply the presence of a plurality of apexes including both one or more peaks and valleys of different heights and depths.

In one particular embodiment, as illustrated in FIG. 3A, the peaks 60, 61 and 62 of each ring 40 are oriented towards the proximal end 46, and the valleys 90, 91 and 92 of each ring 40 are oriented towards the distal end 48. These rings can be positioned in phase relatively to one another, meaning that the peaks of one ring are separated from the peaks of the adjacent ring by one ring width plus the spacing between the rings. Likewise, the valleys of one ring are separated from the valleys of the adjacent ring by one ring width plus the spacing between the rings.

As stated, it may be desirable under certain circumstances to position the peaks so that they are out of phase (not shown), that is, the apexes of the peaks of one ring are circumferentially offset from the apexes of the peaks of an adjacent ring. Positioning the peaks, valleys, and links in this manner, provides a stent having desirable expansion capabilities, high radial strength, a high degree of flexibility, and sufficient wall coverage to support a vessel.

As can be seen, for example, in FIGS. 1-2B, curved portion 56, straight portions 58 have been designed such that when crimped, intermediate peak 62 would nest in the space just distal to the curved portion 56 and straight portions 58. This nesting allows the stent 30 to be tightly crimped onto a delivery system to achieve a low crimped OD.

Referring to FIGS. 2A-2B, the crimping or compressing process, circumferentially moves the undulating link 54 along with its curved portion 56 closer to the intermediate peak 62. Although the various stent struts, curved portions, links, and peaks and valleys may contact each other when the stent is crimped or compressed, it may be desirable to avoid the overlapping of struts 66, 67, 68, apexes 112, and links 54.

Figure 4:
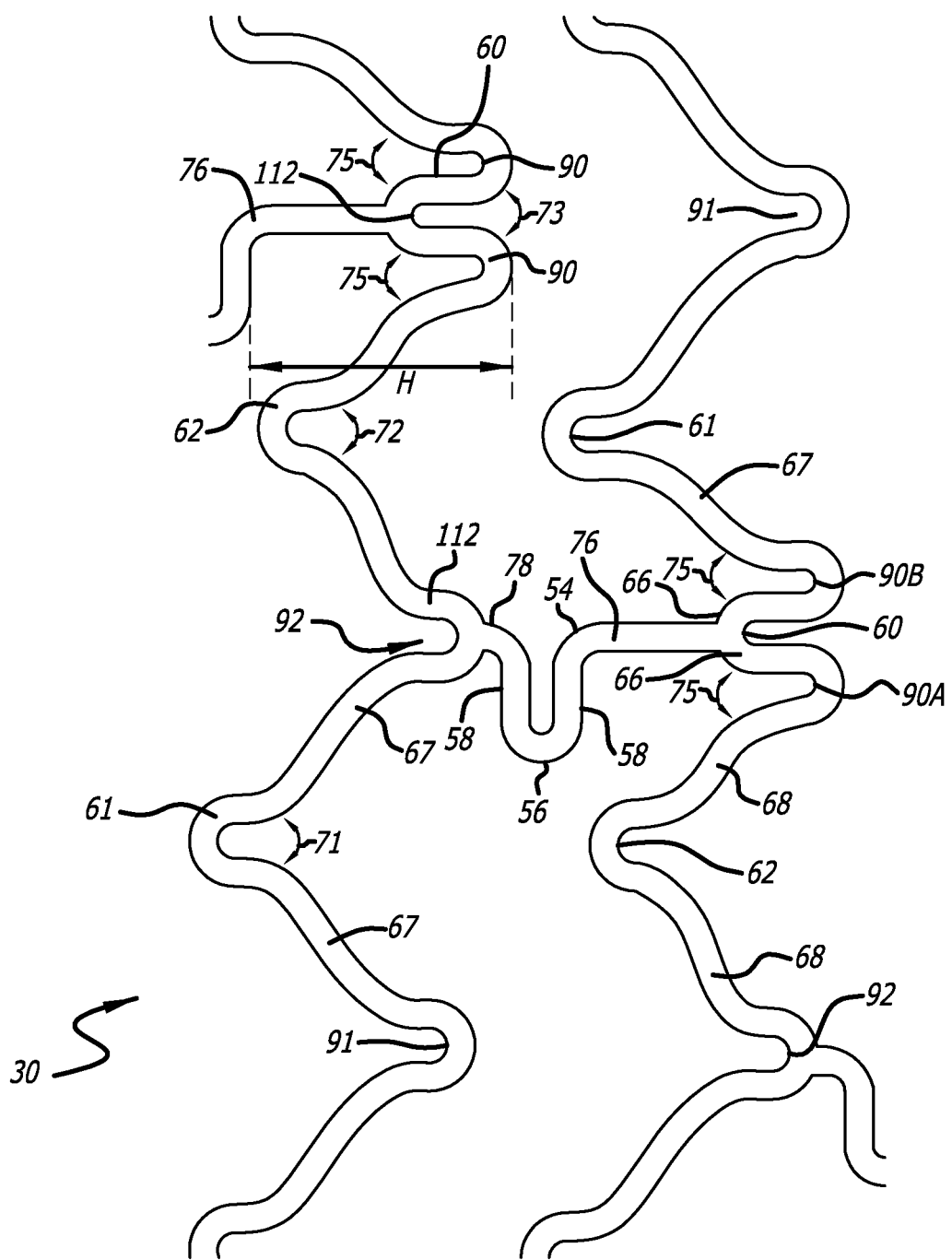
FIG. 4 is an enlarged plan view of a portion of the stent of FIG. 1.

Referring now to FIG. 4, in one embodiment, an arm 76 of the link 54 is attached to the apex 112 of a short peak 60. The length of the arm may vary in different embodiments. The other end 78 of the link 54 is attached to the apex 112 of an intermediate valley 92. Notably, in this embodiment, combined height "H" of the short peak 60 and the arm 76 is longer than the length of the intermediate peak 62 when the stent is in both the compressed and expanded configurations. This allows the stent to be tightly compressed onto a catheter or other stent delivery device, and such structure can be employed to avoid overlapping between the undulating link 54 and the intermediate peak 62. In addition, the circumferential positioning of the intermediate peak 62 and tall peaks 61 can be varied to avoid the intermediate peak 62 and tall peak 61 from touching arm 78 of link 54.

Due to the intricate patterns as disclosed in FIGS. 1-4, the rate of expansion of the various portions of the stent can vary. Accordingly, one aspect of the invention provides for different radii of curvature at various apexes 112 so that the stent will expand evenly and uniformly. Referring more specifically now to FIG. 4, first radius 71 which corresponds with tall peak 61 may have a smaller radius of curvature than does second radius 72 which corresponds with intermediate peak 62. Generally, the longer the struts associated with a peak, the more easily that portion of the stent will expand, so that a smaller radius is associated with peaks having two long struts 67. Likewise, for peaks, such as short peak 60, which has struts 66 that are shorter than the struts 67 of tall peak 61, the apex 112 may have a greater radius 73 of curvature which will expand more easily in order to compensate for the stiffer bending moments created by the shorter struts 66. In yet other embodiments, the radii of curvature of the various peaks and various valleys may be adjusted so that the different types of peaks and valleys expand at different tensions rather than expanding uniformly. In addition, the circumferential positioning of the intermediate peak 62 and tall peaks 61 can be varied to achieve uniform expansion.

The radii 75 of the shallow valleys 90 may also be varied to provide uniform stent expansion. Since a shallow valley formed by an intermediate strut 68 and a short strut 66 can have a tendency to expand more slowly as the stent is expanded compared to a shallow valley formed by a long strut 67 and a short strut 66, a greater radius of a curvature may be incorporated into the shallow valley having the intermediate strut 68. Thus, third radius 75 of a first shallow valley 90A may be greater than the fourth radius 75 of a second adjacent shallow valley 90B. By varying the radii of curvature in the shallow valleys, the stent may expand more evenly and compensate for the varying rates of expansion of adjacent portions in a cylindrical ring.

Figure 5:
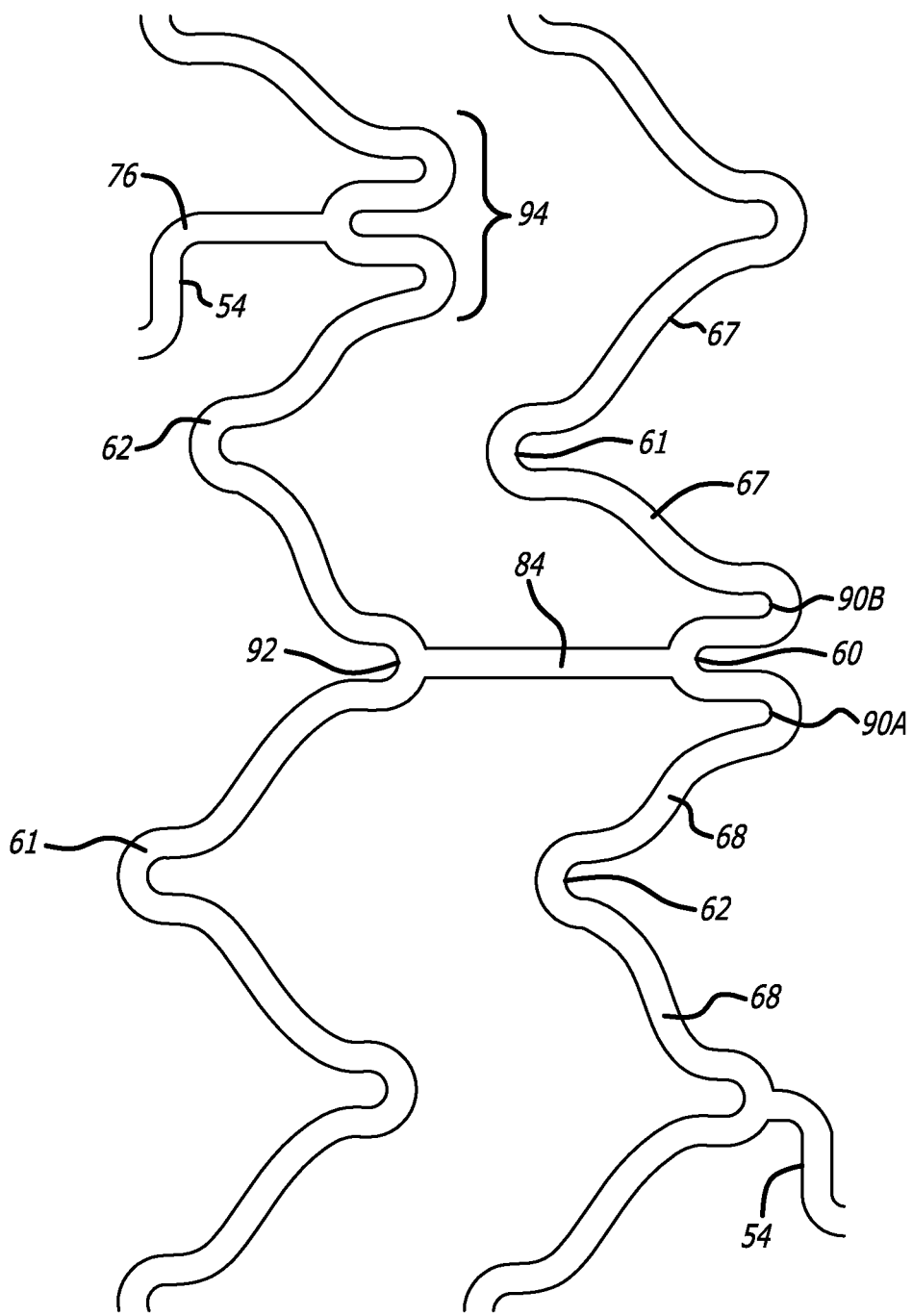
FIG. 5 is an enlarged plan view of a portion of an embodiment of a stent including straight links in an expanded configuration.

Typical stents known in the art undergo a lot of strain as they go from a compressed configuration to an expanded configuration. The strain produced by the expansion of a stent may cause the links to be angulated, resulting in a twisted stent. With reference to FIG. 5, the open W butterfly pattern 94 is shown including two shallow valleys 90 connected with each other by a short peak 60. The butterfly pattern 94 is designed to reduce the strain exerted on the peaks 60, 61, 62, valleys 90, 91, 92, struts 66, 67, 68, and links 54 during expansion of the stent 30. Moreover, the butterfly pattern 94 design facilitates achieving better crimping profiles since the short crest and long crest are positioned further away from the linear link, so during crimping the long crest and short crest have a longer distance to travel before hitting the linear link. It is especially beneficial when the stent is coated with a drug because it prevents or at least minimizes a possibility of coating damage. Moreover, the butterfly W crest increases the stent flexibility since both valleys 90 are two separate components which can move to accommodate any bending when the crimped stent tracks through tortuously.

As previously stated, it is also a design feature that more or fewer links 54 including curved portions be positioned between adjacent cylindrical rings 40. As shown in FIG. 5, straight links 84 in addition to undulating links 54 may be included to connect adjacent cylindrical rings. The straight links can be employed to provide stability and assist in stent length change, as an adjunct to the undulating links.

Further, the straight links may be employed in various alternative approaches to provide more rigidity or flexibility in localized areas, such as greater flexibility at one or both ends and/or more rigidity in the center.

Figure 6:
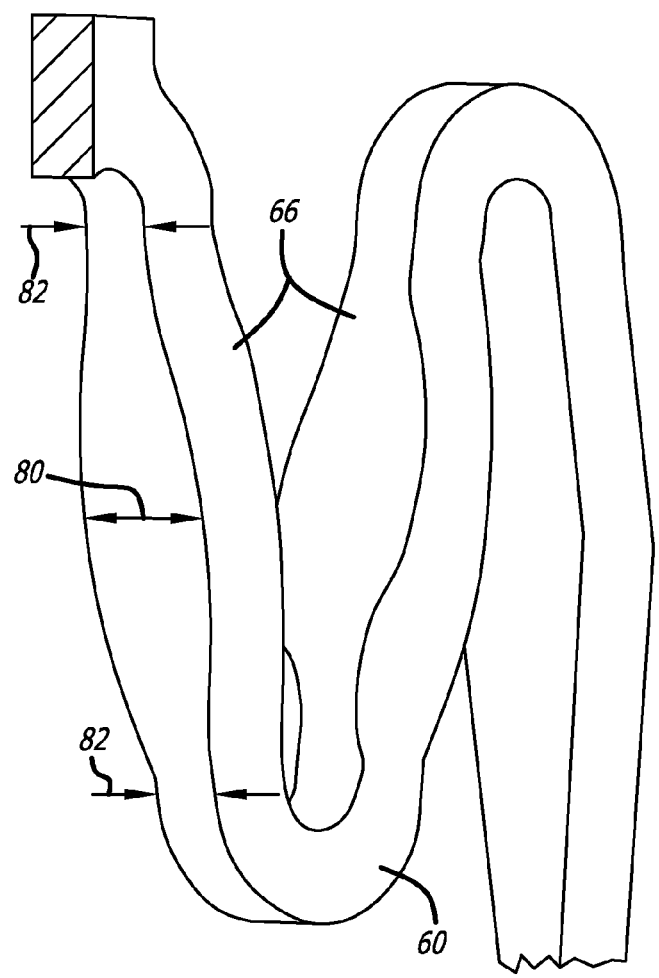
FIG. 6 is an enlarged cutaway perspective view of a portion of an embodiment of a stent having struts with varying radial thickness.

In another aspect of the invention, as shown in FIG. 6, the stent 30 is formed so that the various elements of the cylindrical rings 40, including the long struts 67, short struts 66, intermediate struts 68, various peaks 60, 61, 62, various valleys 90, 91, 92, and the undulating links 54, all can be formed so that each has a variable thickness along the stent length. For example, the undulating link 54 may be thicker at the arm 76 portion than at the extension 78 portion of the link. Such structure can reduce deployment pressure while maintaining radial strength. Further, short struts 66, long struts 67, and intermediate struts 68 may vary in thickness (radial thickness) along their length in order to create variable flexibility in the rings.

Figure 7:
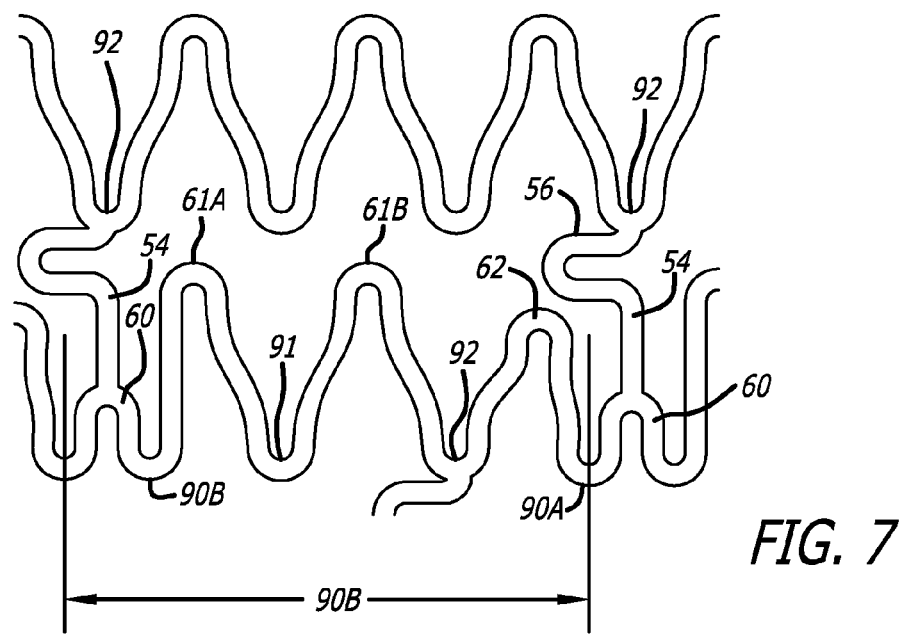
FIG. 7 is an enlarged plan view of a portion of the stent of FIG. 1.
Figure 8:
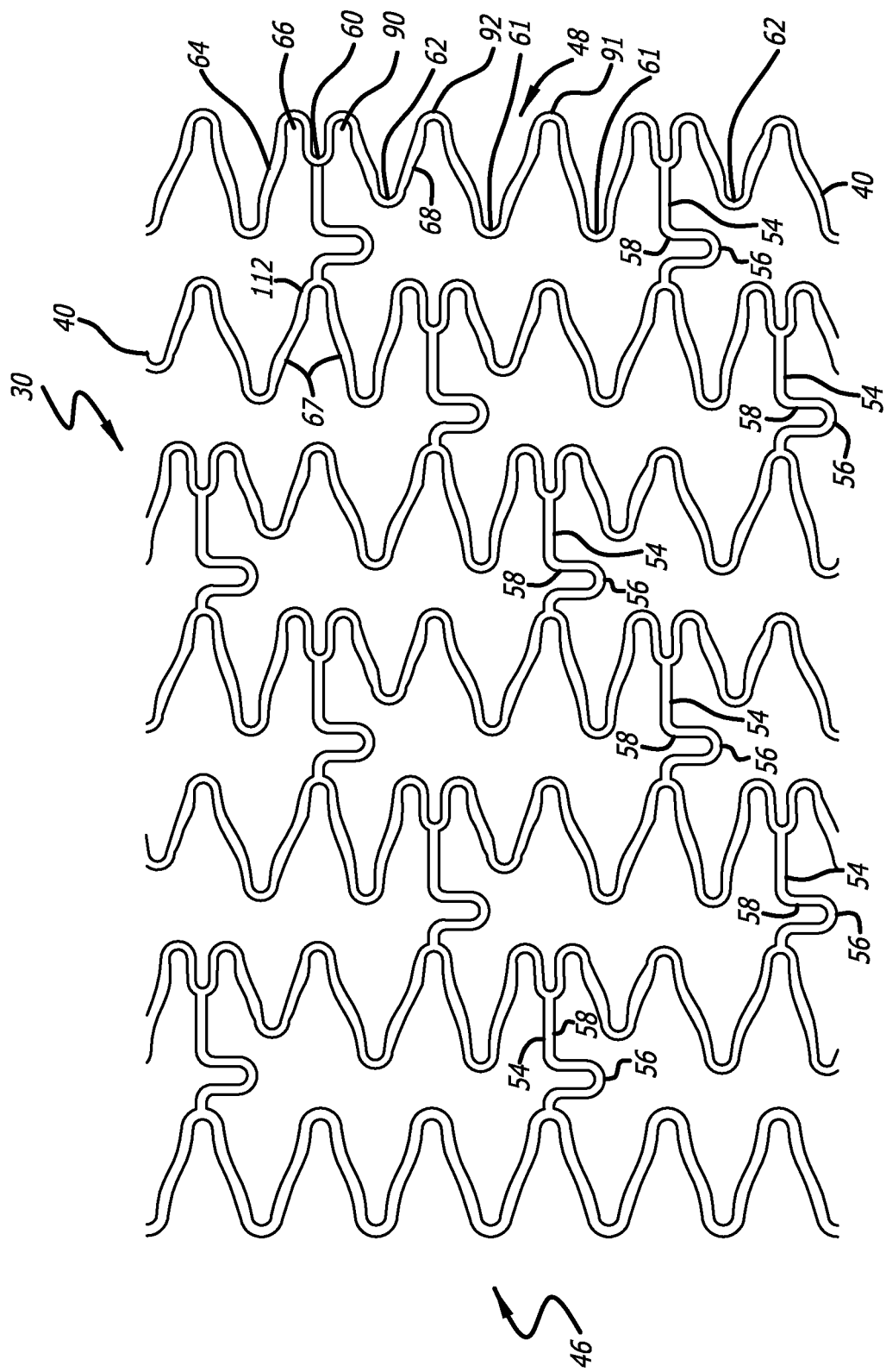
FIG. 8 is a plan view of a portion of a flattened stent of another embodiment of the present invention.

Turning now to FIG. 7, in one contemplated embodiment, at least one cylindrical ring 40 includes a repeating pattern of peaks and valleys. That is, for example, each pattern segment 88 includes in sequence a short peak 60, a shallow valley 90B, a tall peak 61A, a deep valley 91, a tall peak 61B, an intermediate valley 92, an intermediate peak 62, and a shallow valley 90A. The pattern segment may repeat itself as many times as necessary to provide a cylindrical ring of a desired expansion diameter. Also, adjacent cylindrical rings can be connected by one undulating link 54 per pattern segment. For example, an undulating link may connect the short peak 60 of one cylindrical ring to the intermediate valley 92 of an adjacent cylindrical ring. Further, there may be more than one undulating link 54 or straight link 84 (FIG. 5) per pattern segment. In other contemplated embodiments, the links 54, 84 may connect any of the various types of peaks 60, 61, 62 and valleys 90, 91, 92 to any other or same type of peak or valley. Adjacent cylindrical rings can have the same repeating pattern or may have different repeating patterns from each other.

Referring back now to FIG. 1, in one embodiment, the stent of the present invention includes a repeating pattern segment including four peaks and four valleys, and the short peak 60 of a first ring 40A is linked to and longitudinally aligned with the intermediate valley 92 of an adjacent second ring 40B. The short peak 60 of the second ring 40B is linked to and longitudinally aligned with the intermediate valley 92 of an adjacent third ring 40C. In other words, the pattern of the second ring 40B is rotated from the pattern of the first ring 40A, and the pattern of the third ring 40C is further rotated from the pattern of the second ring 40B. This rotational pattern results in the short peaks being longitudinally aligned every third cylindrical ring. Such a three ring longitudinal design may then be repeated as desired to add additional length to a stent. In at least one embodiment, the most proximal end 46A or most distal end 46B of the stent 30 may have a row 40E of undulations having all the same length struts 66, or 67, or 68.

In another embodiment of a stent 30 of the present invention including open W or butterfly pattern of struts (See FIG. 8), substructures of the stent 30 has been rearranged to provide a pattern which addresses potential flaring of ends 46, 48 of the stent. To accomplish this, long struts 67 defining deep valleys 91 are connected to the links 54 and the struts 67, 68 defining the intermediate valley 92 are positioned circumferentially adjacent thereto. In this way, stresses being released from the W or butterfly structure are transferred to a pair of long struts 67 rather than one long strut 67 and one intermediate strut 68.

Further aspects pertaining to stents of the foregoing type are described in U.S. patent application Ser. No. 11/507,852, entitled "Intravascular Stent," which names Diem Ta as the sole inventory and which is incorporated by reference herein in its entirety.

Figure 9:
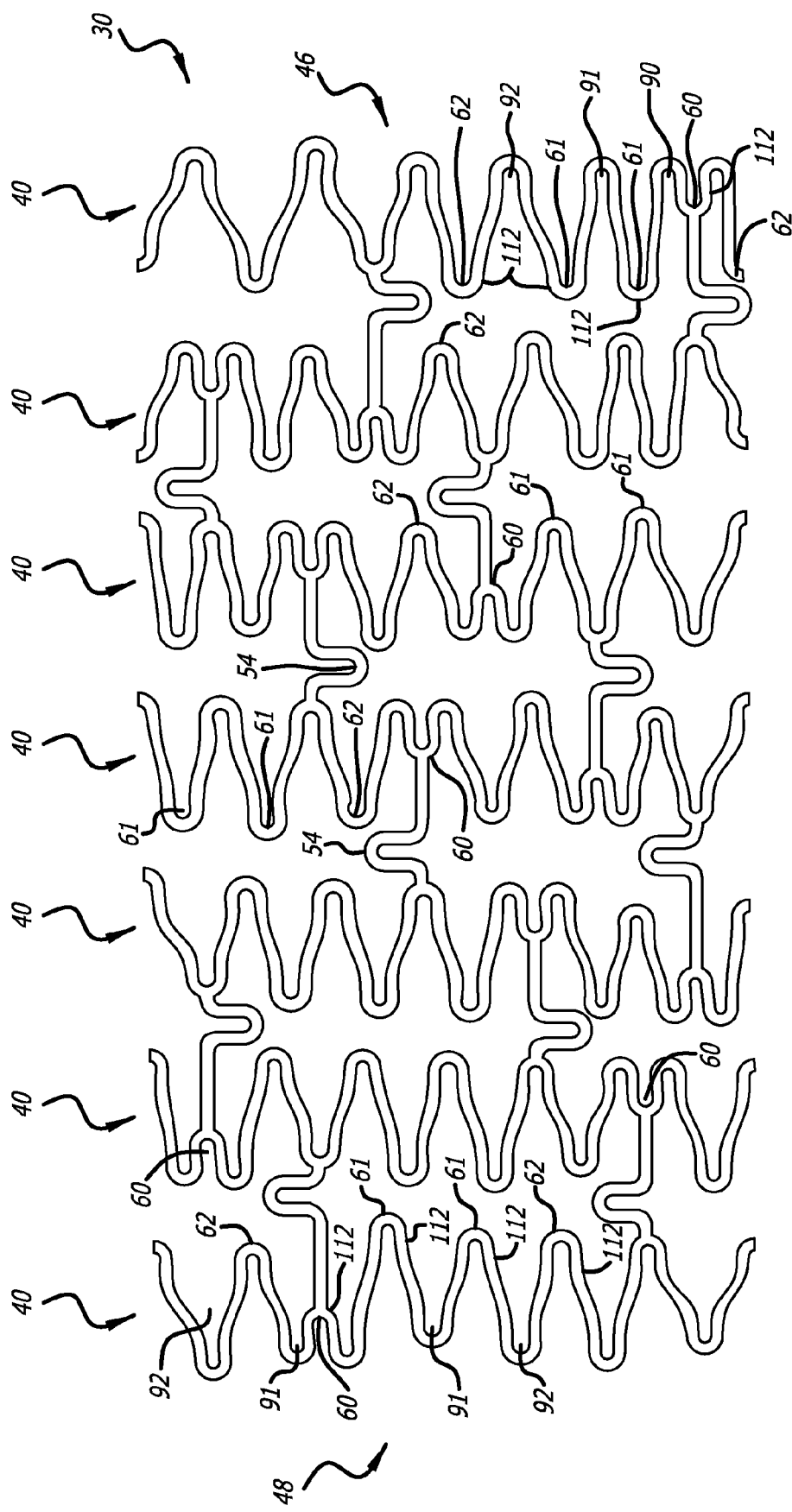
FIG. 9 is a plan view of one embodiment of a non-directional stent in a flattened configuration.

Referring now to FIG. 9, yet another aspect of the stent 30 is embodied in a non-directional stent. Notably, the non-directional stent may be mounted on a delivery device with either the proximal or distal end of the stent oriented towards the distal end of the delivery device with equal effectiveness. Thus, the non-directional stent may be mounted onto a stent delivery system (not shown), for example a balloon catheter, without it being positioned in a preferred proximal-distal orientation. FIG. 9 shows representative features of a portion of the non-directional stent in an as-manufactured (flat) configuration.

In one embodiment of the non-directional stent, all of apexes 112 of the peaks 61, 62 on the most proximal end 46 cylindrical ring 40 of the stent 30 point distally and, all of apexes 112 of the peaks 61, 62 on the most distal end 48 cylindrical ring 40 point proximally. Similarly, all of the valleys 91, 92 of the most distal end 48 ring 40 face proximally, and all of the valleys of the most proximal end 46 ring 40 face distally. Stated another way, all of the peaks on the proximal end 46 ring 40 point towards all of the peaks on the distal end 48 ring 40. Additionally, all of the valleys on the proximal end 46 ring 40 point towards all of the valleys on the distal end 48 ring 40.

In a further aspect, along the entire length of the stent, there may be approximately equal numbers of peaks 61, 62 having apexes 112 that point towards the proximal end 46 of the stent 30 and peaks having apexes that point towards the distal end 48 of the stent. There may also be along the entire length of the stent approximately equal numbers of valleys 91, 92 having apexes 112 that point towards the proximal end 46 of the stent 30 and valleys having apexes that point towards the distal end 48 of the stent.

In still another aspect (not shown), it is contemplated that at least some of the intervening rings 40 that are located between the proximal end 46 and the distal end 48 may include peaks 61, 62 having apexes 112 that point proximally, and some of the other rings may include peaks having apexes that point distally. Similarly, at least some of the intervening rings 40 that are located between the proximal end 46 and the distal end 48 may include valleys 91, 92 having apexes 112 that point proximally, and some of the other rings may include valleys having apexes that point distally. The stent can additionally incorporate the W or butterfly pattern described above.

Moreover, in each of the rings 40 of the stent 30 there may be approximately equal number of peaks 61, 62 having apexes 112 that point towards the proximal end 46 of the stent and peaks having apexes that point towards the distal end 48 of the stent. There may also be in each of the rings of the stent approximately equal number of valleys 91, 92 having apexes that point towards the proximal end of the stent and valleys having apexes that point towards the distal end of the stent.

Furthermore, not all of the apexes 112 of the peaks 61, 62 on one ring 40 need to be aligned in the same direction. For example, some of apexes 112 of the peaks 61, 62 on the ring 40 may point distally 48, and some of the apexes of the peaks on the ring 40 may point proximally 46. Also, some of apexes 112 of the valleys 91, 92 on the ring 40 may point distally 48, and some of the apexes of the valleys on the ring 40 may point proximally 46. Additionally, the rings may be rotationally offset from each other or configured to be in-phase.

In at least one additional embodiment, not all of the curved portions 56 of the undulating links 54 face in the same orientation in the non-directional stent. For example, as shown in FIG. 9, curved portion 56A of undulating link 54A faces in an opposite circumferential direction from curved portion 56B of undulating link 54B.

Additionally, in the non-directional stent, the intermediate struts 68 can be configured to remain adjacent to the curved portions 56 of the undulating links 54. Furthermore, the arm 76 of the undulating link 54 is typically connected to a short peak 60 in the various embodiments of the non-directional stent.

Turning now to another aspect of the invention, a "customized" stent may include customized sections that best meet design requirements for desired stent properties. For example, different pattern designs have benefits specific to the particular pattern design. As a non-limiting illustration, the density of drug coating may be varied to meet particular design requirements. A higher coverage pattern may be useful for even drug distribution.

As another illustration of a "customized" stent design, altering the flexibility of the stent in certain regions can improve deliverability. Stents have traditionally been designed with one pattern throughout the length. In accordance with the present invention, however, the flexibility of the pattern can be altered to meet competing design requirements, such as deliverability and drug distribution.

Different patterns can be combined into one stent, or can be used at different portions of the stent, in order to best meet the customer requirements. Alternatively, the thickness and width of the stent strut can be varied (i.e. variable thickness/width) in order to achieve the desired custom design without changing the entire pattern. As a further alternative, different materials can be fused together in order to achieve the custom requirements.

Figure 10:
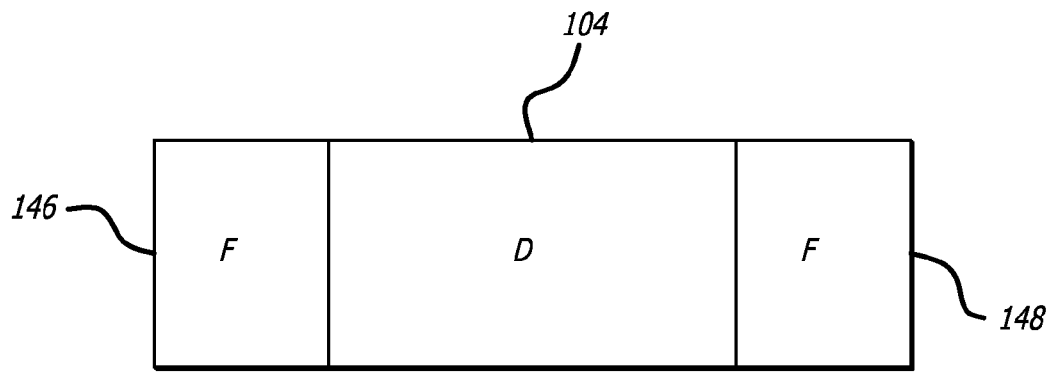
FIG. 10 illustrates properties of a stent having end regions having greater flexibility than the center, and a center region that has more drug coating than the ends.

Considering one embodiment of a "customized" stent design, FIG. 10 depicts in block form a stent that is more flexible at the end portions than in the center, and that has greater drug coverage in the middle that at the ends. The greater flexibility at the ends improves deliverability when the stent is expanded, and the design minimizes edge injury.

The greater number of links in the center portion minimizes "train-wrecking" and "clam-shell opening" effects of prior art stents when the stent is deployed around a curve. Such curved configurations are often found in the body.

Alternative approaches to making the stent more flexible include making the struts thinner and/or narrower at the ends, as desired. Similarly, the dimensions of the link can be increased, such as by increasing the height and/or width of a "U" shaped link. Also, the number of links connecting the rings may be reduced in order to increase flexibility at desired areas of the stent. Increasing the number of turns in the links also improves flexibility.

With respect to varying the drug coating, one approach is to design the areas of the stent that are to have greater drug coating with more surface area than other areas of the stent.

The surface area in a given area may be increased by, for example, making the struts wider or thicker, or by otherwise increasing the surface area of the stent design, such as by increasing the number of links and/or struts in a given region of the stent. The higher drug coverage in the center portion offers a more even drug distribution by minimizing the high and low dose areas.

Another approach with respect to varying the drug coating on the stent is to employ a method of coating the stent that will vary the amount of drug that is coated at a particular location on the stent. For example, if the stent is coated using a spray method, the spray apparatus may be programmed, as with a numerical control system, to vary the density of coating as a function of location on the stent. This may be done by, for example, varying the spray speed along the length of the stent as the stent is being spray coated. Other known methods in the art for applying a coating in a varied fashion may be employed.

Figure 11:
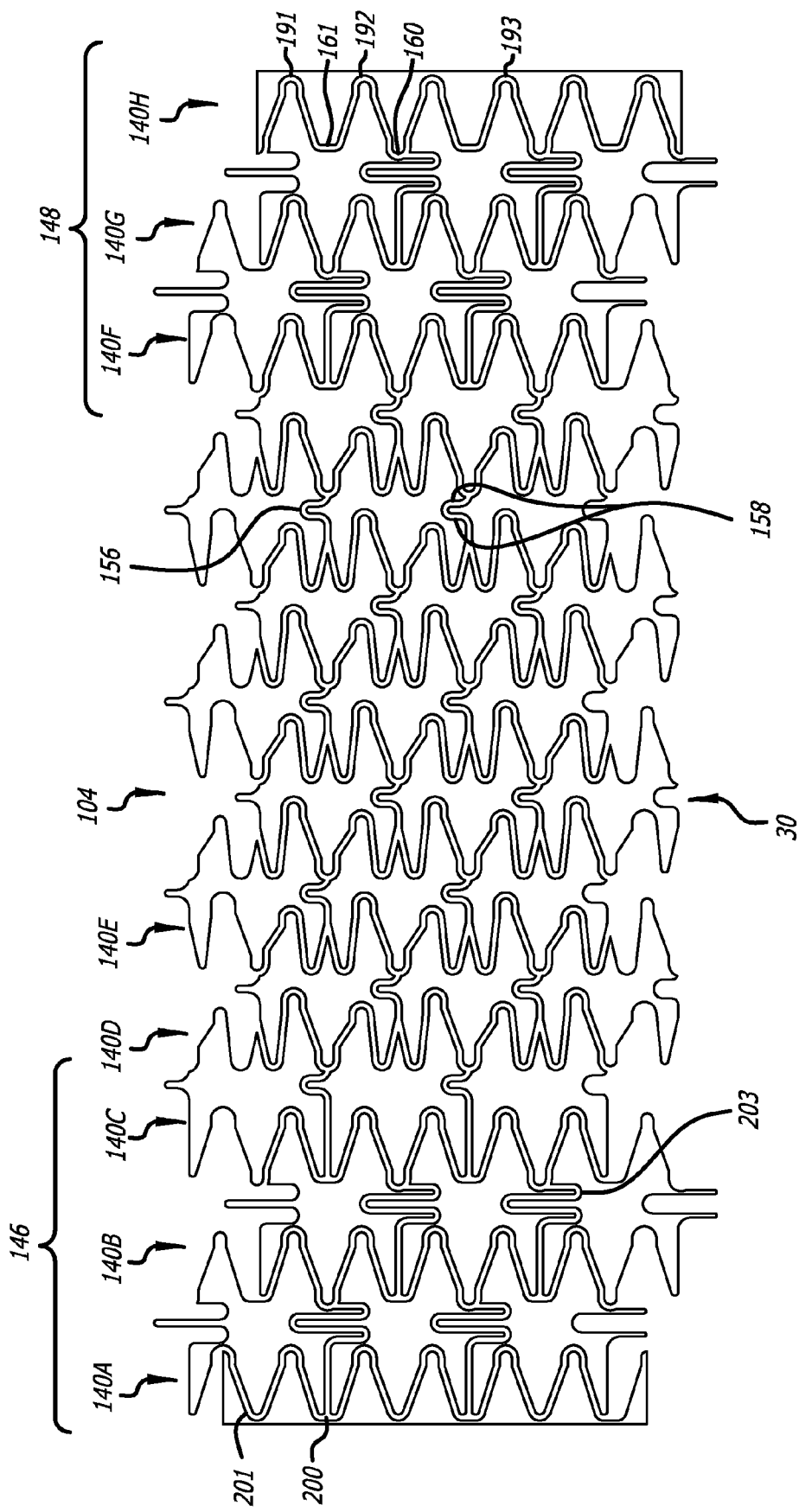
FIG. 11 is a plan view of a portion of a flattened stent having the properties of FIG. 10 and that illustrates a pattern of rings and links.
Figures 12, 13:
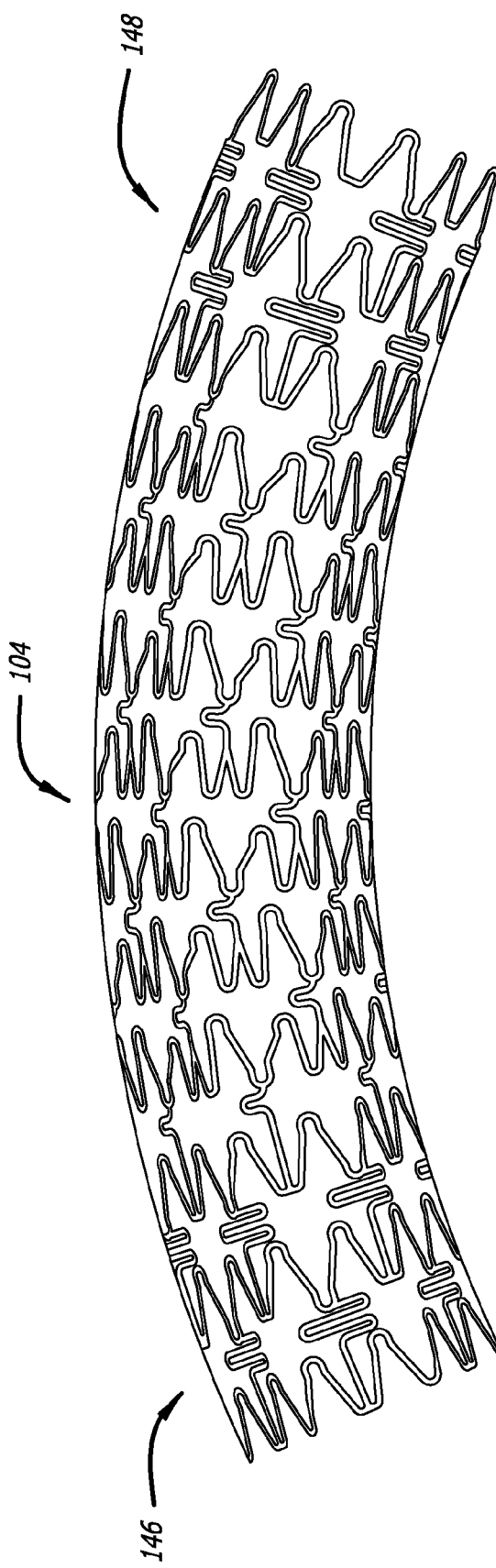
FIG. 12 is a perspective view of the sent of FIG. 11 as it appears deployed in a straight portion of the body.
FIG. 13 is a perspective view of the stent of FIG. 11 as it appears deployed in a curved section of the body.

FIGS. 11-13 depict one non-limiting exemplary design of this type. This design has more flexible ends and greater drug distribution in the middle. FIG. 11 illustrates a stent having flexible distal and proximal ends, 146 and 148, respectively. A center portion 104 extends between the flexible distal and proximal ends 146 and 148. The distal end 146 includes three rings, 140A-C. In ring 140A, for example, there are "U"-shaped members 201 that alternate with "M"-shaped members 200. This pattern is repeated in rings 140B and 140C. The rings of the distal end 146 are interconnected with links 203, which have more turns in the curved section.

The proximal end 148 also has rings 140F-H. Ring 140H, at the far distal end, includes a series of relatively "U"-shaped members, as shown. However, it is noted that the valleys 160 and 162 have a somewhat different shape. The valley 160 has a sharper point, whereas the valley 162 is more squared. These relatively sharp valleys 160 alternate with the relatively squared valleys 162, as shown in FIG. 11. Ring 140G is more like the ring 140A, in that it includes "M"-shaped and "U"-shaped members, which is also true of the ring 140F. The rings 140F through 140H are interconnected with links having more turns in the curved section.

The design of the distal end 146 and the design of the proximal end 148 makes the two ends somewhat more flexible than the center portion 104. The center portion 104 includes rings such as 140D and 140E. The rings have an alternating pattern of links with an open W or butterfly pattern, and links with either straight (not shown) or undulating profile. The rings such as 140D and 140E are interconnected with undulating links.

The net result of the design in FIG. 11 is that the end portions 146 and 148 are more flexible than the center portion 104. This can be advantageous in the body when, for example, the stent is deployed in a sharp curve within the body.

FIG. 12 illustrates the stent of FIG. 11 as it appears in a deployed state but without bending. The flexible distal and proximal ends are illustrated, as is the center portion, which is less flexible than the distal and proximal ends.

FIG. 13 illustrates the stent of FIG. 12 as it appears when bent. The center portion, while flexible, is less flexible than either of the ends. As previously noted, the greater flexibility at the ends improves deliverability when the stent is expanded. The design also minimizes edge injury within the vessel.

Another aspect of the stent of FIGS. 11-13 is the distribution of the drug coating on the stent. The drug coating (not shown) can be concentrated more in the center portion of the stent than on the distal or proximal ends. In the design of FIG. 11, for example, the pattern of the struts and links is such that there is greater surface area in the center portion than on the distal or proximal ends. Consequently, the distribution of the drug coating in the center portion is naturally greater in this design than the distribution of the drug coating on the end portions.

Figure 14:
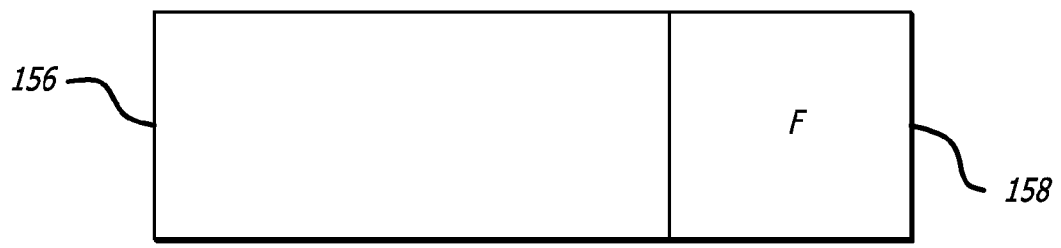
FIG. 14 illustrates properties of a stent having a single end that is more flexible than the rest of the stent.

Turning now to a further alternative design, FIG. 14 depicts in block fashion a design in which a stent has a distal end that is more flexible than one or more other areas of the stent. In one embodiment, the distal end is more flexible than the rest of the stent. This is useful for deliverability, since once the distal end gets through a bend the rest of the stent will be more likely to follow through the bend.

Figure 15:
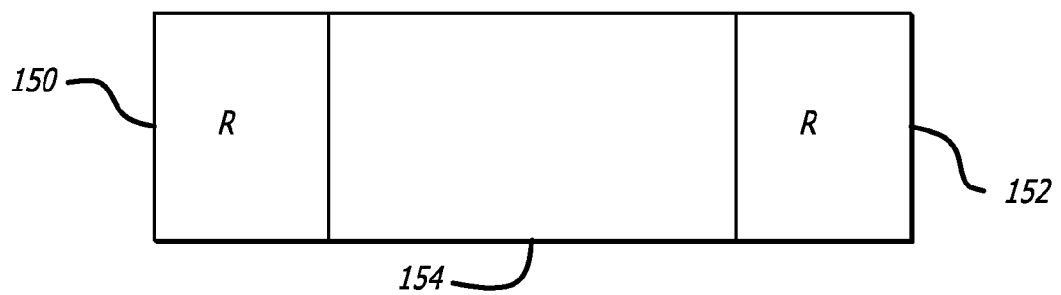
FIG. 15 illustrates properties of a stent having ends that are more radiopaque than the center portion of the stent.

To achieve the result of FIG. 15, the stent design of FIG. 11 may be modified such that the pattern of the center portion 120 is carried out to one of the distal or proximal ends. The remaining end may have the more flexible pattern as shown in FIG. 11. Thus, one end will thereby be more flexible. In this case it will be the distal end that is more flexible, although it must be noted that either pattern of end 100 or 102 may be employed to achieve this greater flexibility.

FIG. 15 depicts in block-diagram fashion a stent with more radiopaque ends. This can simply be achieved by, for example, designing the end rings to have a greater density of metal than other portions of the stent. The greater density of metal may be achieved by increasing the width and/or thickness of struts, links and/or other portions of the stent. Any other method known in the art for increasing radiopaque properties may be employed to achieve a stent with one or both ends being more radiopaque than other areas of the stent.

The stents of FIGS. 10-15 may be used in the same manner as any current stent or drug eluting stent. For example, for arterial stents, the custom stent can be crimped onto a delivery system and delivered through the arteries to a target lesion in the heart. The stent can be deployed by inflating the balloon to the appropriate pressures.

It is noted that this approach can be implemented with stents for various parts of the body, such as with coronary, peripheral, carotid, neuro, and other types of stents. The material can be of stainless steel, CoCr, NiTi, a polymeric stent material, any other material suitable for making stents and known in the art, or any future material developed for stents.

The stent 30 of the present invention can be made in many ways. One method of making the stent is to cut a thin-walled tubular member, such as a stainless steel tubing to remove portions of the tubing in the desired pattern for the stent, leaving relatively untouched the portions of the metallic tubing which are to form the stent. The stent also can be made from other metal alloys such as tantalum, nickel-titanium, cobalt-chromium, titanium, shape memory and superelastic alloys, and the nobel metals such as gold or platinum. In accordance with the invention, it is preferred to cut the tubing in the desired pattern by means of a machine-controlled laser as is well known in the art.

Other methods of forming the stent of the present invention can be used, such as using different types of lasers, chemical etching, electric discharge machining, laser cutting a flat sheet and rolling it into a cylinder, and the like, all of which are well known in the art at this time.

The stent of the present invention also can be made from metal alloys other than stainless steel, such as shape memory alloys. Shape memory alloys are well known and include, but are not limited to, nickel-titanium and nickel-titanium-vanadium. Any of the shape memory alloys can be formed into a tube and laser cut in order to form the pattern of the stent of the present invention. As is well known, the shape memory alloys of the stent of the present invention can include the type having superelastic or thermoelastic martensitic transformation or display stress-induced martensite. These types of alloys are well known in the art and need not be further described here.

The present invention stent is also ideally suited for drug delivery (i.e., delivery of a therapeutic agent) since it has a uniform surface area which ensures uniform distribution of drugs. Typically, a polymer containing the drug is coated onto the stent of the type disclosed in U.S. Pat. Nos. 6,824,559 and 6,783,793 which are incorporated herein by reference.

It is contemplated that the stent 30 of the present invention can be mounted on a stent delivery device or system, for example, a balloon catheter (not shown) similar to those known in the prior art. The stent delivery device includes a distal end for mounting of a stent thereon, and a proximal end configured to remain external to a patient's blood vessel. An example of a stent delivery system is disclosed in U.S. Pat. No. 6,629,994 entitled "INTRAVASCULAR STENT" filed Jun. 11, 2001, the entirety of which is incorporated herein by reference. The present invention, however, is not intended to be limited to delivery using the disclosed stent delivery systems but may be used with other stent delivery systems known in the art. The stent may be tightly compressed or crimped on the balloon portion of the catheter and remains tightly crimped on the balloon during delivery through the patient's vascular system. When the balloon is inflated, the stent expands radially outwardly into contact with the body lumen, for example, a coronary artery. When the balloon portion of the catheter is deflated, the catheter system is withdrawn from the patient, and the stent remains implanted in the artery.

Similarly, if the stent of the present invention is made from a self-expanding metal alloy, such as nickel-titanium or the like, the stent may be compressed onto a catheter, and a sheath (not shown) is placed over the stent to hold it in place until the stent is ready to be implanted in the patient. Such sheaths are well known in the art. Once the stent has been positioned at the intended location, the sheath retracted and the stent self-expands into contact with the wall of the artery. Catheters for self-expanding stents are well known in the art.

It is to be recognized that the invention may be embodied in other forms without departure from the spirit and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention. Accordingly, the scope of the invention is intended to be defined only by reference to the appended claims.

What is claimed:

1. A flexible intravascular stent for use in a body lumen, comprising:
    a plurality of cylindrical rings aligned along a common longitudinal axis; and at least one link connecting adjacent cylindrical rings to form a stent body, the stent body being movable between a delivery configuration and an expanded configuration;
    wherein the stent body has a first end portion, a center portion, and a second end portion, with at least one of the end portions being more flexible than the center portion; and
    the stent body has a drug coating, the drug coating having greater coverage on the center portion than on at least one of the end portions, the center portion including a plurality of cylindrical rings, each cylindrical ring forming the center portion including a plurality of peaks and valleys, each cylindrical ring of the center portion including a plurality of open W-patterns with at least one valley disposed between each open W-pattern, each open W-pattern having a pair of valleys and one U-shaped peak, the peaks of each open W-pattern of a cylindrical ring being longitudinally aligned with the valley portions of an adjacent cylindrical ring, the peak of the open W-pattern having a longitudinal length which is substantially shorter than the longitudinal length of other peaks on the cylindrical ring, the peak of the open W-pattern being connected to one end of the at least one link and the other end of the at least one link being connected to a valley of an adjacent ring, the remainder of the open W-pattern being unconnected to another adjacent ring, wherein each of the at least one link connecting adjacent rings in the center portion includes a curved portion, each of the first end portion and the second end portion including a plurality of cylindrical rings, each cylindrical ring of the first and second end portions being connected by at least one link having at least one more curved portion than the links connecting the cylindrical rings in the center portion, wherein in the first end portion and the second end portion the at least one link connects a valley of one cylindrical ring to a valley of an adjacent cylindrical ring.

2. A flexible intravascular stent as defined in claim 1, wherein both ends are more flexible than the center portion.

3. A flexible intravascular stent as defined in claim 1, wherein at least one cylindrical ring in at least one end portion comprises valleys of uniform extent.

4. A flexible intravascular stent as defined in claim 1, wherein at least one link in the center portion has a "U" profile.

5. A flexible intravascular stent as defined in claim 1, wherein each cylindrical ring includes a plurality of valleys and the at least one link is attached to the peak of the open W-pattern and one of the valleys of an adjacent cylindrical ring.

6. A flexible intravascular stent for use in a body lumen, comprising:
    a plurality of cylindrical rings aligned along a common longitudinal axis; and
    at least one link connecting adjacent cylindrical rings to form a stent body, the stent body being movable between a delivery configuration and an expanded configuration;
    wherein the stent body has a first end portion, a center portion, and a second end portion and
    at least one of the end portions is more radiopaque than the center portion, the center portion including a plurality of cylindrical rings, each cylindrical ring forming the center portion including a plurality of peaks and valleys, each cylindrical ring including a plurality of open W-patterns with at least one valley disposed between each open W-pattern, each open W-pattern having a pair of valleys and one U-shaped peak, the peak of the open W-pattern having a longitudinal length which is substantially shorter than the longitudinal length of other peaks on the cylindrical ring, the peaks of each open W-pattern of a cylindrical ring being longitudinally aligned with the valley portions of an adjacent cylindrical ring, the peak of the open W-pattern being connected to one end of the at least one link and the other end of the at least one link being connected to a valley of an adjacent ring, the remainder of the open W-pattern being unconnected to another adjacent ring, wherein each of the at least one links connecting adjacent rings in the center portion includes a curved portion, each of the first end portion and the second end portion including a plurality of cylindrical rings, each cylindrical ring of the first and second end portions being connected by at least one link having at least one more curved portion than the links connecting the cylindrical rings in the center portion, wherein in the first end portion and the second end portion the at least one link connects a valley of one cylindrical ring to a valley of an adjacent cylindrical ring.

7. A flexible intravascular stent as defined in claim 6, wherein the stent body comprises metal, at least one of the end portions has more metal than the center portion.

8. A flexible intravascular stent as defined in claim 6, wherein both the first end portion and the second end portion are more radiopaque than the center portion.

9. A flexible intravascular stent as defined in claim 6, wherein at least one of the first end portion and the second end portion have a surface area density greater than the center portion.

10. A flexible intravascular stent as defined in claim 6, wherein both the first end portion and the second end portion have a surface area density greater than the center portion.

11. A flexible intravascular stent as defined in claim 6, wherein at least one of the first end portion and the second end portion is relatively more flexible than the center portion.

12. A flexible intravascular stent for use in a body lumen, comprising:
   a plurality of cylindrical rings aligned along a common longitudinal axis; and
   at least one link connecting adjacent cylindrical rings to form a stent body, the stent body being movable between a delivery configuration and an expanded configuration;
   wherein the stent body has a first end portion, a center portion, and a second end portion; and
   at least one of the end portions is more flexible than the center portion, the center portion including a plurality of cylindrical rings, each cylindrical ring forming the center portion including a plurality of peaks and valleys, each cylindrical ring including a plurality of open W-patterns with at least one valley disposed between each open W-pattern, each open W-pattern having a pair of valleys and one U-shaped peak, the peak of each open W-pattern of a cylindrical ring being longitudinally aligned with a valley portion of an adjacent cylindrical ring, the peak of the open W-pattern having a longitudinal length which is substantially shorter than the longitudinal length of other peaks on the cylindrical ring, the peak of the open W-pattern being connected to one end of the at least one link and the other end of the at least one link being connected to a valley of an adjacent ring, the remainder of the open W-pattern being unconnected to another adjacent ring, wherein each of the at least one links connecting adjacent rings in the center portion includes a curved portion, each of the first end portion and the second end portion including a plurality of cylindrical rings, each cylindrical ring of the first and second end portions being connected by at least one link having at least one more curved portion than the links connecting the cylindrical rings in the center portion, wherein in the first end portion and the second end portion the at least one link connects a valley of one cylindrical ring to a valley of an adjacent cylindrical ring.

13. A flexible intravascular stent as defined in claim 12, wherein the center portion has more drug coating such that the coating than the end portions.

14. A flexible intravascular stent as defined in claim 12, wherein both ends are more flexible than the center portion.

15. A flexible intravascular stent as defined in claim 12, wherein at least one link in one of the end portions has a multiple turns.

16. A flexible intravascular stent as defined in claim 12, wherein at least one link in each of the end portions has a multiple turns.

17. A flexible intravascular stent as defined in claim 12, wherein at least one cylindrical ring in at least one end portion comprises valleys of uniform extent.

18. A flexible intravascular stent as defined in claim 12, wherein at least one link in the center portion has a "U" profile.

* * * * *